United States Patent [19]

Quinby

[11] 4,224,610
[45] Sep. 23, 1980

[54] ALARM DEVICE FOR DRAINAGE POUCH

[76] Inventor: James D. Quinby, 1092 NE. Glass Dr., Jensen Beach, Fla. 33457

[21] Appl. No.: 933,377

[22] Filed: Aug. 14, 1978

Related U.S. Application Data

[63] Continuation of Ser. No. 688,633, May 21, 1976, abandoned.

[51] Int. Cl.² ............................................. G08B 21/00
[52] U.S. Cl. ............................... 340/614; 128/214 E; 340/573; 340/668; 128/295
[58] Field of Search ............... 340/668, 604, 614, 573; 128/275, 283, 295, 214 E; 200/DIG. 2

[56] References Cited

U.S. PATENT DOCUMENTS

| 2,930,031 | 3/1960 | Ungar | 340/626 |
|---|---|---|---|
| 3,121,864 | 2/1964 | Bowman | 340/546 |
| 3,582,935 | 6/1971 | Verhaeghe | 340/668 X |
| 3,670,320 | 6/1972 | Palmer | 340/668 X |
| 3,968,485 | 7/1976 | DeHart | 340/545 |
| 4,069,817 | 1/1978 | Fenole et al. | 340/604 X |
| 4,106,001 | 8/1978 | Mahoney | 340/604 |

OTHER PUBLICATIONS

Autogenous Oxygenation, etc. by Holt et al.; Oct., 1960, p. 539.

Primary Examiner—John W. Caldwell, Sr.
Assistant Examiner—Daniel Myer
Attorney, Agent, or Firm—Witherspoon & Hargest

[57] ABSTRACT

An alarm device to be attached to an enterostomy incontinence drainage pouch which will provide warning when said pouch becomes filled. A miniaturized alarm is attached to the drainage pouch by clamp means. A cable is secured to the actuating mechanism of the miniaturized alarm and is attached across the drainage pouch in such a way that the outward expansion of the pouch when it becomes filled will exert a force against the cable, causing the alarm to be actuated.

3 Claims, 3 Drawing Figures

FIG. 1.
FIG. 2.
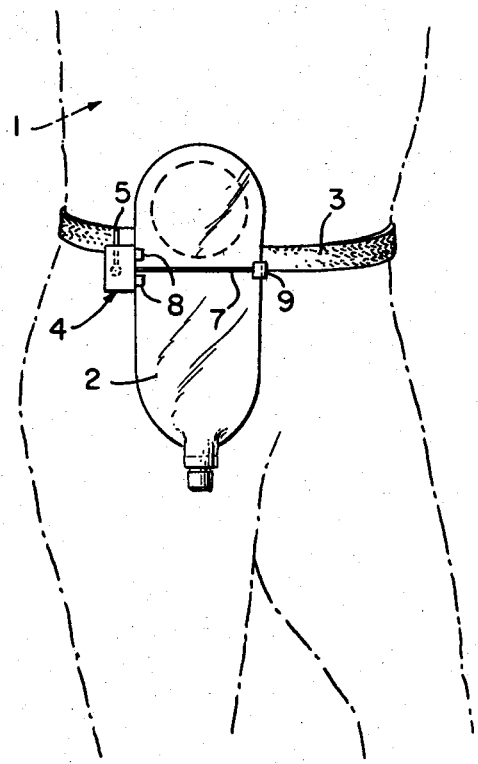
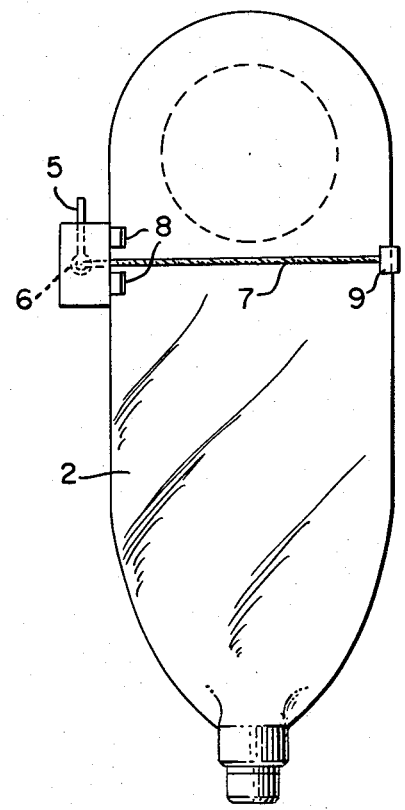
FIG. 3.
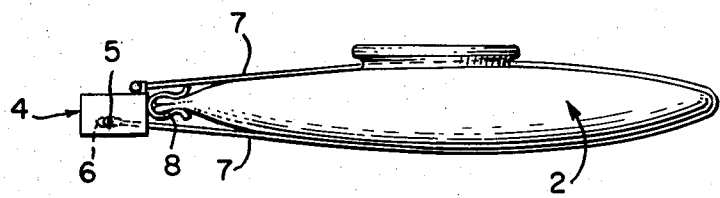

ALARM DEVICE FOR DRAINAGE POUCH

This is a continuation of application Ser. No. 688,633 filed May 21, 1976, now abandoned.

BACKGROUND OF THE INVENTION

1. Field of the Invention

This invention relates generally to medical appliances and more particularly to an alarm device used in conjunction with enterostomy appliances adapted to collect drainage from an incontinent patient.

2. Description of the Prior Art

In many instances of incontinence a patient will use a drainage pouch to collect bodily fluid discharges, with the pouch secured to his body by supporting means. As an example, it is sometimes necessary to bypass the functioning of patient's bladder or portion of intestine and directly draw the urine produced by the kidneys out of the body through an artificial opening, or "stoma", formed in the abdominal region by surgical procedures. Conventional appliances utilize a drainage pouch which may be connected to the stoma to collect the urine discharged. This pouch is normally constructed of a relatively thin rubber or plastic flexible material which will bend and flex with the body movements of the patient. The pouch can be connected directly to the stoma using an adhesive with additional strap means or other supporting means to aid in holding the pouch in position. Leakage of the urine can occur about the point of connection which can cause discomfort for the patient and difficulties from a sanitary standpoint as well. Leakage potential, of course, becomes particularly acute when the pouch becomes filled. Often, the patient may have reduced sensitivity caused by nerve damage which inhibits his awareness of the incontinence appliance and its operation. The patient may not immediately become aware of such leakage with sanitary and comfort problems resulting. Conventional appliances offer no convenient method of checking the level of fluid that has been collected other than by feeling the pouch. The pouch is normally covered by clothing which will make checking by feeling less convenient and, in addition, the patient will often not think of checking the level due to his preoccupation with other matters.

SUMMARY OF THE INVENTION

It is a principle object of the present invention to provide an alarm device for a drainage pouch of an enterostomy incontinence appliance which will provide a signal to the patient when the pouch becomes full, thus reminding the patient to empty the pouch and thereby preventing the discomfort and sanitary problems which may accompany any spill-over that may occur after the pouch becomes full.

It is a further object to provide an alarm device for a drainage pouch of an enterostomy incontinence appliance which may be easily transferred from one drainage pouch to another.

Yet further objects of the present invention are to provide an alarm device for a drainage pouch of an enterostomy incontinence appliance which is simple in design, inexpensive to manufacture, easy to use, and efficient in operation.

BRIEF DESCRIPTION OF THE DRAWING

FIG. 1 is a view of a drainage pouch attached to a patient;

FIG. 2 is a front plan view of the drainage pouch with the alarm device attached illustrating the principle features of the alarm device which is considered the invention; and FIG. 3 is a top plan view illustrating an alternative cable arrangement wherein the cable encircles the drainage pouch.

DETAILED DESCRIPTION OF THE INVENTION

Referring now to the drawing, FIG. 1 shows a person 1 wearing an enterostomy drainage pouch 2 which is directly connected to the stoma of the wearer and is held in place by a belt 3. Pouch 2 represents any conventional stoma connected type of enterostomy pouch available on the market. The apparatus of this invention is utilized in connection with such conventional pouches.

Referring now to both FIGS. 1 and 2, these Figures show a first embodiment of the alarm system of this invention. As shown in FIGS. 1 and 2, this first embodiment comprises a miniaturized alarm device 4, a cable 7 and the clamps 8 and 9 used to attach miniaturized alarm 4 and cable 7, respectively, to pouch 2.

Miniaturized alarm device 4 is any suitable small alarm device that is either battery powered or operated by a hand wound spring device. Many alarm devices suitable for use as alarm device 4 are available on the market. For example, alarm device 4 may be a simple battery operated buzzer or an alarm wrist watch modified to sound an alarm at any time upon actuation or may be any other type of small device capable of providing an audible alarm upon actuation. As will become apparent, alarm device 4 need not produce a very loud sound. In fact, alarm device 4 need not provide an audible alarm. Alarm device 4 could merely be a vibrator. The wearer would sense the vibrations without anyone else knowing that alarm device 4 has been actuated. Alarm device 4 is provided with an actuating mechanism or switch 5 which is provided to turn alarm device 4 "on" and "off".

Alarm device 4 is attached to pouch 2 by the clamping means 8. Clamping means 8 is any suitable clamping means that will secure alarm device 4 to pouch 2 without rupturing pouch 2.

Cable 7 is placed across pouch 2 and has its one end secured to actuating mechanism 5 and its other end secured to pouch 2 by means of the clamp 9. Clamp 9 is any suitable clamp that will hold this end of cable 7 in place without rupturing pouch 2.

In order to secure the one end of cable 7 to actuating mechanism 5, actuating mechanism 5 may be conveniently provided with an eyelet 6 formed at one end thereof. Eyelet 6 is given by way of example only as being a convenient way of securing cable 7 to actuating mechanism 5. How this one end of cable 7 is secured to actuating mechanism 5 of a given alarm device 4 will depend upon the construction of actuating mechanism 5 and the manner in which it is operated.

The apparatus of FIGS. 1 and 2 operates in the following manner: the apparatus is assembled and attached to pouch 2 in the manner described above when the pouch is empty. The length of cable 7 is such that this cable fits snugly across pouch 2 when pouch 2 is empty.

When fluid enters pouch 2, pouch 2 expands outwardly since it is made of a flexible material. As pouch 2 becomes full or nearly full, it expands outwardly in the area of cable 7. This outward expansion of pouch 2 in the area of cable 7 causes cable 7 to move outward thereby pulling on actuating mechanism 5 to move from the "off" position to the "on" position. When actuating mechanism 5 is turned "on", alarm device 4 emits an audible signal thereby warning the user of pouch 2 that pouch 2 is full or nearly full. The user of pouch 2 then turns actuating mechanism 5 to the "off" position and empties pouch 2. If, for any reason, pouch 2 is replaced with a new pouch, the alarm apparatus is merely detached from the old pouch and attached to the new pouch.

FIG. 3 shows a variation of the embodiment of the invention shown in FIGS. 1 and 2. Like parts in the various figures have the same numerals. The only difference between the embodiment of FIG. 3 and the embodiment shown in FIGS. 1 and 2 is that cable 7 completely surrounds pouch 2 and has one end fastened to alarm device 4 at the point 10 as indicated in FIG. 3, the other end of cable 7 being attached to actuating mechanism 5. The operation of the embodiment of FIG. 3 is identical to the operation of the embodiment shown in FIGS. 1 and 2.

While the invention is shown as being used with the type of pouch that is directly connected to the stoma, it should be obvious that the alarm system of this invention can also be used with the conventional leg carried drainage pouch. In other words, the alarm system of this invention can be used with any type of conventional drainage pouch. Furthermore, while the invention has been shown and described with reference to two specific embodiments, it will be obvious to those skilled in the art that various changes and modifications can be made to these embodiments without departing from the spirit and scope of the invention as set forth in the claims.

What is claimed is:

1. An alarm device for an incontinence appliance comprising a drainage pouch constructed of a flexible material, said alarm device comprising:
   a miniaturized self-contained signalling device having an "on"-"off" switch for turning said miniaturized self-contained signallind device "on" and "off", said miniaturized self-contained signalling device emitting an alarm signal when turned "on" and being quiescient when turned "off" by said "on"-"off" switch; clamping means for detachably securing said miniaturized self-contained signalling device directly to one side of said drainage pouch;
   a cable having a first end and a second end, said cable being so positioned relative to said pouch such that said cable is in contact with the outer surface of said drainage pouch;
   means to secure said first end of said cable to said "on"-"off" switch, and
   means to secure said second end of said cable, relative to said drainage pouch and said miniaturized self-contained signalling device, in such a manner that said cable exerts a pulling force on said "on"-"off" switch to turn said "on"-"off" switch to its "on" position when said drainage pouch becomes filled to approximately its maximum capacity, thereby causing said signalling device to emit an alarm signal indicating that said drainage pouch has become filled to approximately its maximum capacity.

2. An alarm device as defined in claim 1 wherein said means to secure said second end of said cable comprises clamping means for detachably securing said second end of said cable to the side of said drainage pouch opposite the side of said drainage pouch to which said signalling device is secured, said cable extending across one outside surface of said drainage pouch.

3. An alarm device as defined in claim 1 wherein said cable surrounds said drainage pouch and said means to secure said second end of said cable comprises means to secure said second end of said cable to said signalling device.

* * * * *